(12) United States Patent
Tanaka

(10) Patent No.: US 10,834,791 B2
(45) Date of Patent: Nov. 10, 2020

(54) LIGHT SOURCE DEVICE

(71) Applicant: OLYMPUS CORPORATION, Tokyo (JP)

(72) Inventor: Satoshi Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/357,661

(22) Filed: Mar. 19, 2019

(65) Prior Publication Data

US 2019/0215925 A1 Jul. 11, 2019

Related U.S. Application Data

(63) Continuation of application No. PCT/JP2017/031744, filed on Sep. 4, 2017.

(30) Foreign Application Priority Data

Dec. 12, 2016 (JP) .................................. 2016-240382

(51) Int. Cl.
*H05B 45/22* (2020.01)
*A61B 1/06* (2006.01)
(Continued)

(52) U.S. Cl.
CPC .......... *H05B 45/22* (2020.01); *A61B 1/00009* (2013.01); *A61B 1/0638* (2013.01);
(Continued)

(58) Field of Classification Search
CPC . A61B 1/00009; A61B 1/0638; A61B 1/0684; G02B 23/24; G02B 6/0035;
(Continued)

(56) References Cited

U.S. PATENT DOCUMENTS

2008/0246927 A1* 10/2008 Inoue ..................... G09G 3/002
353/85
2008/0303410 A1* 12/2008 Kaneda ................. H01L 33/504
313/503
(Continued)

FOREIGN PATENT DOCUMENTS

EP        2130484 A1    12/2009
JP     2009-131324 A     6/2009
(Continued)

OTHER PUBLICATIONS

International Search Report dated Oct. 17, 2017 issued in PCT/JP2017/031744.

*Primary Examiner* — Amy Cohen Johnson
*Assistant Examiner* — Syed M Kaiser
(74) *Attorney, Agent, or Firm* — Scully, Scott, Murphy & Presser, P.C.

(57) ABSTRACT

A light source device includes: a first light emitting element configured to generate first light having intensity in a first wavelength band and having a first optical spectrum; a second light emitting element configured to generate second light having intensity in a second wavelength band adjoining to the first wavelength band and having a second optical spectrum overlapping with a part of the first optical spectrum; and a processor configured to, at a time of causing the first light emitting element and the second light emitting element to simultaneously perform light emission, cause the first light to be generated with a light amount adjusted according to a first mixed light amount which is a light amount of the second light mixed in the first wavelength band.

12 Claims, 5 Drawing Sheets

(51) Int. Cl.
 *G02B 23/24* (2006.01)
 *G06T 11/00* (2006.01)
 *A61B 1/00* (2006.01)
(52) U.S. Cl.
 CPC ............ *A61B 1/0684* (2013.01); *G02B 23/24* (2013.01); *G06T 11/001* (2013.01)
(58) Field of Classification Search
 CPC .... G02B 6/0036; G02B 6/0038; G02B 6/004; G02B 6/0043; H05B 45/22; H05B 47/10; H05B 47/11; H05B 47/135; H05B 47/155
 See application file for complete search history.

(56) References Cited

U.S. PATENT DOCUMENTS

| | | | |
|---|---|---|---|
| 2009/0306478 A1 | 12/2009 | Mizuyoshi | |
| 2012/0133928 A1* | 5/2012 | Urano | G01N 21/9501 356/237.2 |
| 2012/0242219 A1* | 9/2012 | Seo | C07D 409/10 313/504 |
| 2013/0113911 A1* | 5/2013 | Hanano | G02B 21/16 348/79 |
| 2013/0155723 A1* | 6/2013 | Coleman | G02B 6/0011 362/621 |
| 2013/0278645 A1* | 10/2013 | Liu | G09G 3/3607 345/690 |
| 2013/0293156 A1* | 11/2013 | Wells | F21V 23/003 315/312 |
| 2015/0160542 A1* | 6/2015 | Tomiyama | G03B 21/2033 353/31 |
| 2015/0261078 A1* | 9/2015 | Tomiyama | G03B 21/2033 353/20 |
| 2015/0287366 A1* | 10/2015 | Miyamoto | G03B 21/2033 345/690 |
| 2015/0316775 A1* | 11/2015 | Hsieh | G03B 21/2013 353/31 |
| 2015/0335232 A1* | 11/2015 | Ito | G02B 23/26 362/13 |
| 2016/0040833 A1* | 2/2016 | Zehetner | H01L 25/075 362/84 |
| 2016/0091151 A1* | 3/2016 | Itoi | G02B 6/0023 362/612 |
| 2016/0273717 A1* | 9/2016 | Krames | A61M 21/00 |
| 2016/0337565 A1* | 11/2016 | Long | G03B 15/05 |
| 2016/0363710 A1* | 12/2016 | Van Boven | F21S 8/04 |
| 2016/0381759 A1* | 12/2016 | Watanabe | H05B 45/24 315/297 |
| 2017/0014022 A1* | 1/2017 | Tamura | A61B 1/00009 |
| 2017/0089758 A1* | 3/2017 | Okamoto | H04N 9/3155 |
| 2017/0124943 A1* | 5/2017 | Peana | G09G 3/3225 |
| 2017/0343792 A1* | 11/2017 | Matsunobu | G02B 27/1006 |
| 2018/0173087 A1* | 6/2018 | Hsieh | G03B 21/2033 |
| 2018/0261160 A1* | 9/2018 | Wu | H01L 27/3262 |
| 2019/0142240 A1* | 5/2019 | Hayashi | A61B 1/045 |

FOREIGN PATENT DOCUMENTS

| | | |
|---|---|---|
| JP | 2009-297290 A | 12/2009 |
| JP | 2015-179291 A | 10/2015 |
| JP | 5855619 B2 | 2/2016 |

* cited by examiner

LIGHT SOURCE DEVICE

CROSS REFERENCE TO RELATED APPLICATION

This application is a continuation application of PCT/JP2017/031744 filed on Sep. 4, 2017 and claims benefit of Japanese Application No. 2016-240382 filed in Japan on Dec. 12, 2016, the entire contents of which are incorporated herein by this reference.

BACKGROUND OF THE INVENTION

1. Field of the Invention

The present invention relates to a light source device, and in particular to a light source device used for observation of living tissue.

2. Description of the Related Art

In endoscopic observation in a medical field, as a method for adjusting color balance of lights of a plurality of colors radiated to an object such as living tissue in a body cavity, for example, a method of adjusting a light amount ratio among the lights of the plurality of colors has been conventionally known.

More specifically, for example, Japanese Patent Application Laid-Open Publication No. 5855619 discloses such a configuration that, in an endoscope system capable of performing observation in a plurality of observation modes, a light amount ratio among lights of a plurality of colors emitted from a plurality of LEDs provided in a light source device, respectively, is adjusted, referring to a light adjustment table created for each observation mode.

SUMMARY OF THE INVENTION

A light source device of an aspect of the present invention includes: a first light emitting element configured to generate first light having intensity in a first wavelength band and having a first optical spectrum; a second light emitting element configured to generate second light having intensity in a second wavelength band adjoining to the first wavelength band and having a second optical spectrum overlapping with a part of the first optical spectrum; and a processor configured to, at a time of causing the first light emitting element and the second light emitting element to simultaneously perform light emission, cause the first light to be generated with a light amount adjusted according to a first mixed light amount which is a light amount of the second light mixed in the first wavelength band.

DETAILED DESCRIPTION OF THE PREFERRED EMBODIMENT(S)

An embodiment of the present invention will be described below with reference to drawings.

FIGS. 1 to 8 relate to the embodiment of the present invention.

Figure 1:
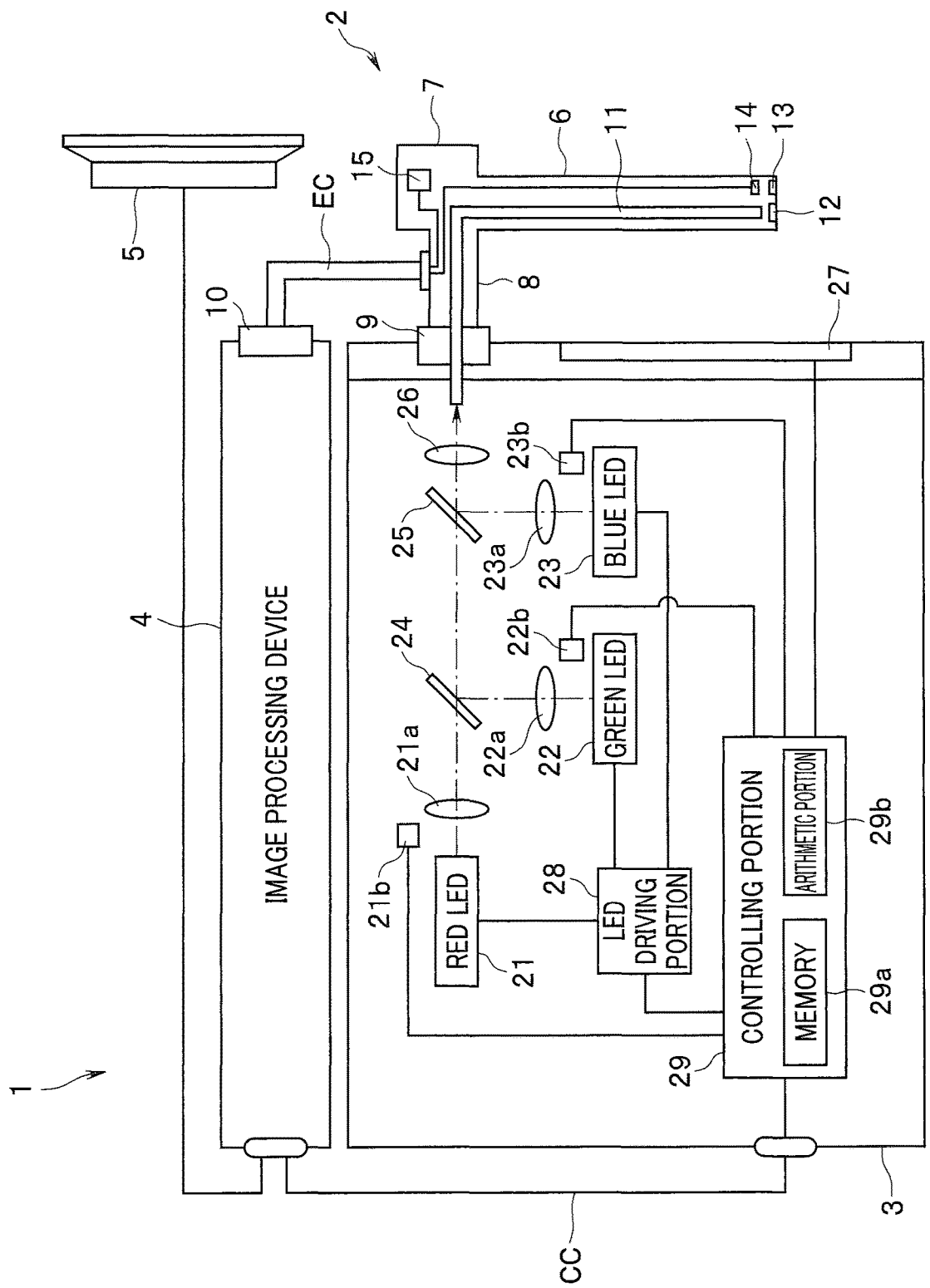
FIG. 1 is a diagram showing a configuration of main parts of an endoscope system including a light source device according to an embodiment.

As shown in FIG. 1, an endoscope system 1 has an endoscope 2 configured to pick up an image of an object inside a subject such as a living body and output an image pickup signal, a light source device 3 configured to supply illumination light for illuminating the object to the endoscope 2, an image processing device 4 configured to generate and output an image based on the image pickup signal outputted from the endoscope 2, and a monitor 5 configured to display the image outputted from the image processing device 4. The light source device 3 and the image processing device 4 are connected via a communication cable CC. FIG. 1 is a diagram showing a configuration of main parts of the endoscope system including the light source device according to the embodiment.

The endoscope 2 is configured having an elongated insertion portion 6 insertable into an inside of an object, an operation portion 7 formed on a proximal end portion of the insertion portion 6, a universal cable 8 provided extending from the operation portion 7, an optical connector 9 provided on an end portion of the universal cable 8 and an electrical connector 10 provided on an end portion of an electrical cable EC branched from the universal cable 8.

The operation portion 7 is configured in a shape that a user such as a surgeon can grasp to operate the operation portion 7. The operation portion 7 is provided with one or more scope switches (not shown) capable of giving an instruction corresponding to an operation by the user to the image processing device 4.

The optical connector 9 is configured to be detachably connected to a connector receptacle (not shown) of the light source device 3.

The electrical connector 10 is configured to be detachably connected to a connector receptacle (not shown) of the image processing device 4.

The endoscope 2 is configured having a light guide 11 configured to transmit illumination light supplied from the light source device 3 to which the optical connector 9 is connected, an illumination lens 12 arranged on an optical path of the illumination light emitted from the light guide 11, an objective lens 13 configured to form an optical image of an object illuminated by the illumination light emitted via the illumination lens 12, an image pickup device 14 configured to pick up an optical image formed by the objective lens 13 and output an image pickup signal and a memory 15 in which light amount ratio information to be described later is stored.

The light guide 11 is inserted inside the insertion portion 6, the operation portion 7 and the universal cable 8. An incident end portion of the light guide 11 including a light incident surface is provided extending from the optical connector 9. An emitting end portion of the light guide 11 including a light emitting surface is arranged near the light incident surface of the illumination lens 12.

The image pickup device 14 is configured being provided with an image sensor such as a color CCD or a color CMOS. The image pickup device 14 is configured to photoelectrically convert an optical image formed by the objective lens 13 to generate an image pickup signal and output the generated image pickup signal to the image processing device 4 to which the electrical connector 10 is connected.

In the memory 15, light amount ratio information LIA is stored, which is information about a light amount ratio among respective lights (R light, G light and B light to be described later) emitted from the light source device 3 set in advance according to the kind of the endoscope 2 and the like.

The image processing device 4 is configured, for example, being provided with an image processing circuit. The image processing device 4 is configured to calculate a ratio of an average luminance of an image generated based on an image pickup signal outputted from the endoscope 2 to a predetermined target luminance and output brightness control information showing the calculated ratio to the light source device 3. That is, the brightness control information is information acquired according to brightness of an image at the time of picking up an image of an object illuminated by the R light, the G light and the B light to be described later. The image processing device 4 is also configured, for example, to read the light amount ratio information from the memory 15 and output the read light amount ratio information to the light source device 3 when the image processing device 4 is powered up.

The light source device 3 is configured to be capable of supplying, for example, the R light which is red light, the G light which is green light and the B light which is blue light as illumination light for illuminating an object.

The light source device 3 is configured having a red LED 21 provided with a function as a light emitting portion configured to generate the R light, a lens 21a configured to condense and emit the R light, and an optical sensor 21b arranged near the red LED 21 and configured to detect an emitted light amount of the R light of the red LED 21, and generate and output a light amount detection signal showing the detected emitted light amount.

The light source device 3 is configured having a green LED 22 provided with a function as a light emitting portion configured to generate the G light, a lens 22a configured to condense and emit the G light, and an optical sensor 22b arranged near the green LED 22 and configured to detect an emitted light amount of the G light of the green LED 22, and generate and output a light amount detection signal showing the detected emitted light amount.

The light source device 3 is configured having a blue LED 23 provided with a function as a light emitting portion configured to generate the B light, a lens 23a configured to condense and emit the B light, and an optical sensor 23b arranged near the blue LED 23 and configured to detect an emitted light amount of the B light of the blue LED 23, and generate and output a light amount detection signal showing the detected emitted light amount.

Figure 2:
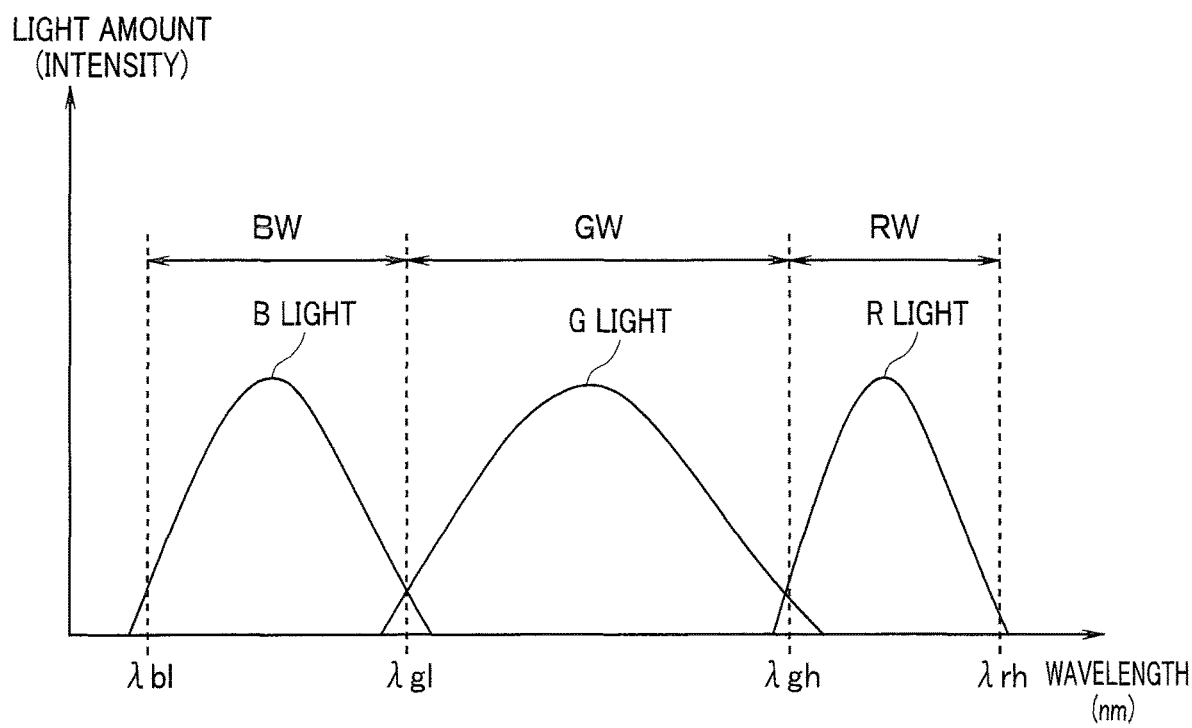
FIG. 2 is a diagram showing an example of optical spectra of lights emitted from respective LEDs provided in the light source device according to the embodiment.

Note that, in the present embodiment, description will be made on an assumption that the R light having intensity in a wavelength band RW of wavelengths from $\lambda gh$ to $\lambda rh$ is emitted from the red LED 21, the G light having intensity in a wavelength band GW of wavelengths from $\lambda gl$ to $\lambda gh$ is emitted from the green LED 22, and the B light having intensity in a wavelength band BW of wavelengths from Xbl to $\lambda gl$ is emitted from the blue LED 23, for example, as shown in FIG. 2. In the present embodiment, description will be made on an assumption that an optical spectrum of the R light emitted from the red LED 21 and an optical spectrum of the G light emitted from the green LED 22 mutually overlap near the wavelength $\lambda gh$, and the optical spectrum of the G light emitted from the green LED 22 and an optical spectrum of the B light emitted from the blue LED 23 mutually overlap near the wavelength $\lambda gl$, for example, as shown in FIG. 2. In the present embodiment, description will be made on an assumption that the wavelength bands RW and GW adjoin to each other, and the wavelength bands GW and BW adjoin to each other, for example, as shown in FIG. 2. It is assumed that each of the wavelengths ($\lambda bl$, $\lambda gl$, $\lambda gh$ and $\lambda rh$) defining the wavelength bands RW, GW and BW is a set value that is set, for example, according to the model of the light source device 3 and the like. FIG. 2 is a diagram showing an example of the optical spectra of the lights emitted from respective LEDs provided in the light source device according to the embodiment.

The light source device 3 is configured having a dichroic mirror 24 configured being provided with such an optical characteristic that causes the R light emitted via the lens 21a to be transmitted to the connector receptacle side and causes the G light emitted via the lens 22a to be reflected to the connector receptacle side.

The light source device 3 is configured having a dichroic mirror 25 configured being provided with such an optical characteristic that causes the R light and the G light emitted via the dichroic mirror 24 to be transmitted to the connector receptacle side and causes the B light emitted via the lens 23a to be reflected to the connector receptacle side.

The light source device 3 is configured having a lens 26 configured to condense the R light, the G light and the B light emitted via the dichroic mirror 25 and emit the R light, the G light and the B light to the light incident surface of the light guide 11 arranged near the connector receptacle when the optical connector 9 is connected.

The light source device 3 has an operation panel 27 configured with a user interface such as switches capable of giving an instruction corresponding to an operation by the user to a controlling portion 29.

The light source device 3 has an LED driving portion 28 configured to generate and output an LED driving signal for driving each of the red LED 21, the green LED 22 and the blue LED 23 in response to control by the controlling portion 29. The LED driving portion 28 is configured, for example, being provided with an LED driving circuit for generating the LED driving signal.

The light source device 3 has the controlling portion 29 configured to be capable of performing control related to adjustment of light amounts of the R light, G light and the B light, for the LED driving portion 28 based on the brightness control information outputted from the image processing device 4, a light amount detection signal outputted from each of the optical sensors 21b, 22b and 23b and light source control information to be described later.

The controlling portion 29 is configured, for example, being provided with a CPU. The controlling portion 29 is also configured to be capable of performing control for causing each of the red LED 21, the green LED 22 and the blue LED 23 to perform light emission or extinction, for the LED driving portion 28 in response to an instruction from the operation panel 27. The controlling portion 29 is configured having a memory 29a and an arithmetic portion 29b.

The memory 29a stores R sensor characteristic information which is information showing a correlation between an emitted light amount value of the red LED 21 in a case where only the red LED 21 among the respective LEDs provided in the light source device 3 is caused to perform light emission alone and an R sensor detection value obtained according to a light amount of the R light detected by the optical sensor 21b. The memory 29a stores R sensor correction information that is used to correct the R sensor characteristic information described above to obtain RLED (red LED) control information.

The memory 29a stores G sensor characteristic information which is information showing a correlation between an emitted light amount value of the green LED 22 in a case where only the green LED 22 among the respective LEDs provided in the light source device 3 is caused to perform light emission alone and a G sensor detection value obtained according to a light amount of the G light detected by the optical sensor 22b. The memory 29a stores G sensor correction information that is used to correct the G sensor characteristic information described above to obtain GLED (green LED) control information.

The memory 29a stores B sensor characteristic information which is information showing a correlation between an emitted light amount value of the blue LED 23 in a case where only the blue LED 23 among the respective LEDs provided in the light source device 3 is caused to perform light emission alone and a B sensor detection value obtained according to a light amount of the B light detected by the optical sensor 23b. The memory 29a stores B sensor correction information that is used to correct the B sensor characteristic information described above to obtain BLED (blue LED) control information.

The memory 29a stores light amount ratio information LIB for setting the light amount ratio among the R light, the G light and the B light to a predetermined light amount ratio.

The arithmetic portion 29b is configured to, by reading the R sensor characteristic information and the R sensor correction information stored in the memory 29a and correcting the R sensor characteristic information using the read R sensor correction information and light amount ratio information LIT, which is either the light amount ratio information LIA or LIB, acquire RLED control information. The arithmetic portion 29b is configured to, by reading the G sensor characteristic information and the G sensor correction information stored in the memory 29a and correcting the G sensor characteristic information using the read G sensor correction information and the light amount ratio information LIT, which is either the light amount ratio information LIA or LIB, acquire GLED control information. The arithmetic portion 29b is configured to, by reading the B sensor characteristic information and the B sensor correction information stored in the memory 29a and correcting the B sensor characteristic information using the read B sensor correction information and the light amount ratio information LIT, which is either the light amount ratio information LIA or LIB, acquire BLED control information. The arithmetic portion 29b is configured to acquire the RLED control information, the GLED control information and the BLED control information as light source control information.

Next, an operation and the like of the endoscope system 1 of the present embodiment will be described.

By operating the operation panel 27 after connecting and powering up each portion of the endoscope system 1, the user instructs the controlling portion 29, for example, to supply white light including the R light, G light and the B light to the endoscope 2 as illumination light.

When the light source device 3 is powered up, the arithmetic portion 29b performs an operation for comparing a light amount ratio R1 shown by the light amount ratio information LIA outputted from the image processing device 4 and a light amount ratio R2 shown by the light amount ratio information LIB stored in the memory 29a.

If the arithmetic portion 29b obtains a comparison result that the light amount ratios R1 and R2 correspond to each other, the arithmetic portion 29b corrects each piece of sensor characteristic information using one of the light amount ratios R1 and R2. If the arithmetic portion 29b obtains a comparison result that the light amount ratios R1 and R2 do not correspond to each other, the arithmetic portion 29b corrects each piece of sensor characteristic information using the light amount ratio R1. If the arithmetic portion 29b cannot compare the light amount ratios R1 and R2, for example, because the light amount ratio information LIA is not stored in the memory 15, the arithmetic portion 29b corrects each piece of sensor characteristic information using the light amount ratio R2.

That is, if the arithmetic portion 29b cannot acquire the light amount ratio information LIA for setting the light amount ratio among the R light, the G light and the B light to the light amount ratio R1 different from the light amount ratio R2, from the image processing device 4, the arithmetic portion 29b corrects each piece of sensor characteristic information using the light amount ratio R2. If the arithmetic portion 29b can acquire the light amount ratio information LIA for setting the light amount ratio among the R light, the G light and the B light to the light amount ratio R1 different from the light amount ratio R2, from the image processing device 4, the arithmetic portion 29b corrects each piece of sensor characteristic information using the light amount ratio R1.

Here, description will be made below on a specific example of a method for acquiring the sensor characteristic information and the sensor correction information of each sensor stored in the memory 29a. Note that, hereafter, description will be made on a case where the light amount ratio among the R light, the G light and the B light is set to $\alpha:1:\beta$, that is, a case where the light amount of the R light is set $\alpha$ times as large as the light amount of the G light, and the light amount of the B light is set $\beta$ times as large as the light amount of the G light, as an example. Hereinafter, for simplification, a method for acquiring the G sensor characteristic information and the G sensor correction information stored in the memory 29a will be described as a representative example.

For example, at a time of manufacture or shipment inspection of the light source device 3, a factory operator gives an instruction for causing an operation related to acquisition of the G sensor characteristic information to be performed, to the controlling portion 29, by operating the operation panel 27 in a state that an actinometer (not shown) provided with a function of capable of detecting a light amount (intensity) of incident light in a visible region for each 1 nm wavelength and acquiring an optical spectrum is connected to the connector receptacle of the light source device 3.

In response to the instruction from the operation panel 27, the controlling portion 29 performs control for causing only the green LED 22 to perform light emission alone with the minimum light amount value Lmin, for the LED driving portion 28 and performs an operation for acquiring a G sensor detection value DGA corresponding to a light amount detection signal outputted from the optical sensor 22b. Further, in response to the instruction from the operation panel 27, the controlling portion 29 performs control for causing only the green LED 22 to perform light emission alone with the maximum light amount value Lmax, for the LED driving portion 28, and performs an operation for acquiring a G sensor detection value DGB corresponding to a light amount detection signal outputted from the optical sensor 22b.

Note that the minimum light amount value Lmin corresponds, for example, to a lower limit of a light amount that can be set by operating the operation panel 27. Note that the maximum light amount value Lmax corresponds, for example, to an upper limit of the light amount that can be set by operating the operation panel 27.

The arithmetic portion 29b acquires G sensor characteristic information showing a correlation between an emitted light amount value LG of the green LED 22 in the case where only the green LED 22 is caused to perform light emission alone and a G sensor detection value DG obtained according to a light amount of the G light detected by the optical sensor 22b, based on the G sensor detection value DGA acquired with the minimum light amount value Lmin and the G sensor detection value DGB acquired with the maximum light amount value Lmax, and stores the acquired G sensor characteristic information into the memory 29a.

Figure 3:
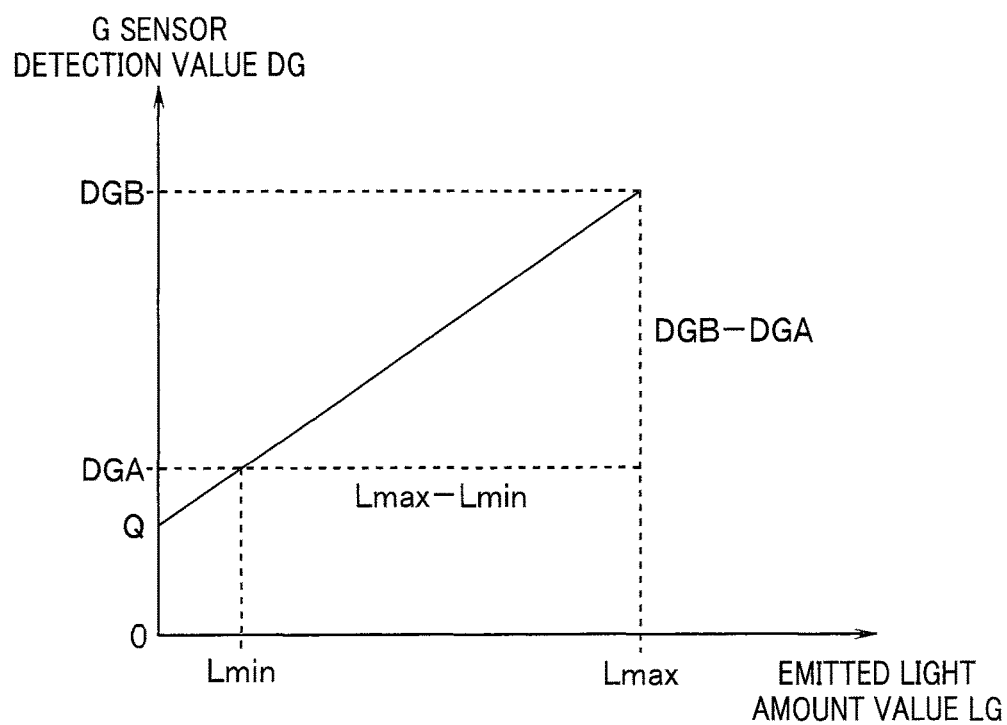
FIG. 3 is a diagram showing an example of G sensor characteristic information of the light source device according to the embodiment.

That is, according to the operation of the arithmetic portion 29b as described above, a relational expression showing that the G sensor detection value DG linearly changes relative to the emitted light amount value LG is stored into the memory 29a as the G sensor characteristic information, for example, as shown by an equation (1) below and in FIG. 3. FIG. 3 is a diagram showing an example of the G sensor characteristic information of the light source device according to the embodiment.

$$DG = A \times LG + Q \tag{1}$$

Note that an inclination A included in the right side of the above equation (1) is, for example, a value calculated by performing arithmetic operation of (DGB−DGA)/(Lmax−Lmin) (see FIG. 3). An intercept Q included in the right side of the above equation (1) is, for example, a value determined according to electrical characteristics of the optical sensor 22b such as a dark current.

For example, by further operating the operation panel 27 after giving an instruction for causing the operation related to acquisition of the G sensor characteristic information to be performed, the factory operator gives an instruction for causing each of R light with the minimum light amount value Lmin and R light with the maximum light amount value Lmax to be generated for a predetermined time period.

Figure 4:
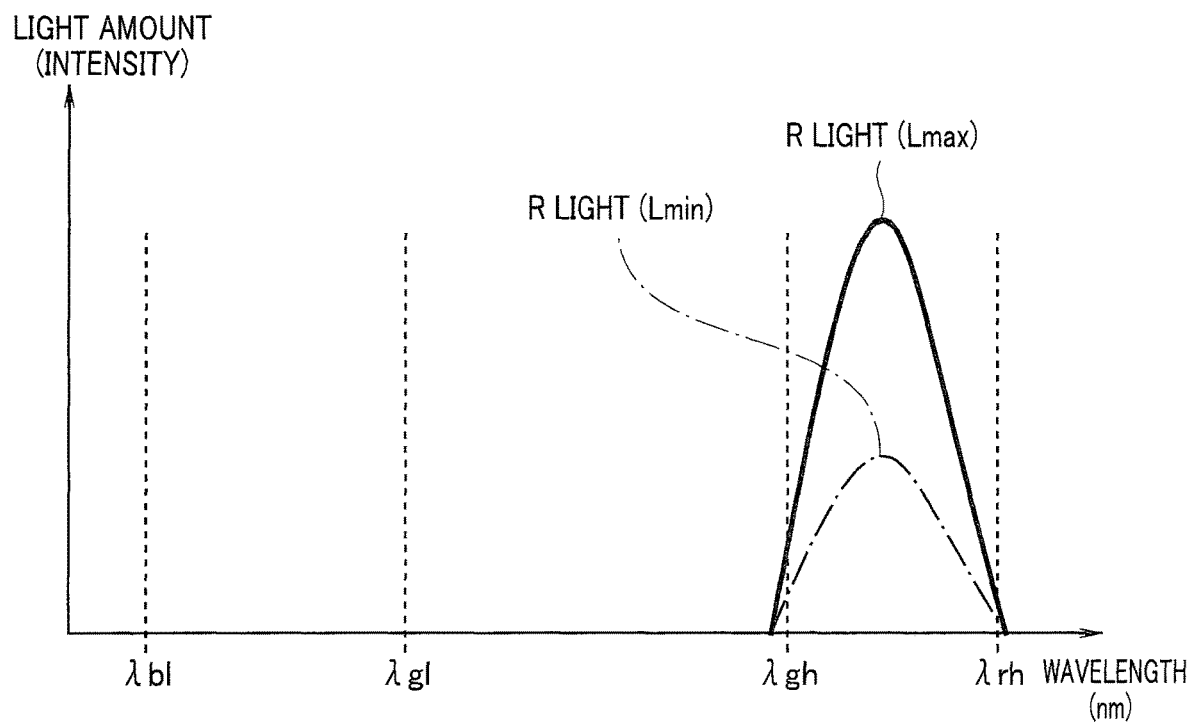
FIG. 4 is a diagram showing an example of optical spectra acquired when a red LED provided in the light source device according to the embodiment is caused to perform light emission with a minimum light amount value Lmin and a maximum light amount value Lmax, respectively.

In response to the instruction from the operation panel 27, the controlling portion 29 performs control, for example, for causing the red LED 21 to perform light emission alone with the minimum light amount value Lmin for a predetermined time period after causing the red LED 21 to perform light emission alone with the minimum light amount value Lmin for a predetermined time period, for the LED driving portion 28. In response to such an operation of the controlling portion 29, for example, an optical spectrum as shown by a long dashed short dashed line in FIG. 4 is acquired by the actinometer as an optical spectrum of the R light at the time of causing the red LED 21 to perform light emission alone with the minimum light amount value Lmin. In response to such an operation of the controlling portion 29, for example, an optical spectrum as shown by a bold line in FIG. 4 is acquired by the actinometer as an optical spectrum of the R light at the time of causing the red LED 21 to perform light emission alone with the maximum light amount value Lmax. FIG. 4 is a diagram showing an example of the optical spectra acquired when the red LED provided in the light source device according to the embodiment is caused to perform light emission with the minimum light amount value Lmin and the maximum light amount value Lmax, respectively.

For example, by further operating the operation panel 27 after giving an instruction for causing the operation related to acquisition of the G sensor characteristic information to be performed, the factory operator gives an instruction for causing each of B light with the minimum light amount value Lmin and B light with the maximum light amount value Lmax to be generated for a predetermined time period.

Figure 5:
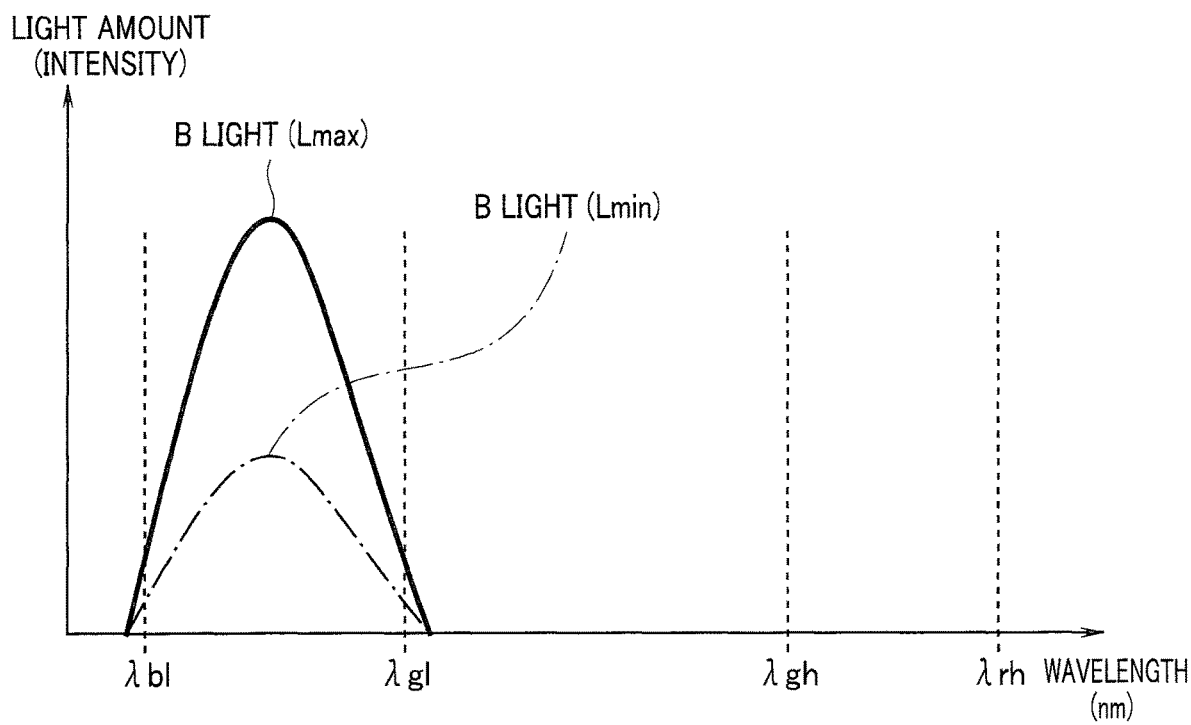
FIG. 5 is a diagram showing an example of optical spectra acquired when a blue LED provided in the light source device according to the embodiment is caused to perform light emission with the minimum light amount value Lmin and the maximum light amount value Lmax, respectively.

In response to the instruction from the operation panel 27, the controlling portion 29 performs control, for example, for causing the blue LED 23 to perform light emission alone with the maximum light amount value Lmax for a predetermined time period after causing the blue LED 23 to perform light emission alone with the minimum light amount value Lmin for a predetermined time period, for the LED driving portion 28. In response to such an operation of the controlling portion 29, for example, an optical spectrum as shown by a long dashed short dashed line in FIG. 5 is acquired by the actinometer as an optical spectrum of the B light at the time of causing the blue LED 23 to perform light emission alone with the minimum light amount value Lmin. In response to such an operation of the controlling portion 29, for example, an optical spectrum as shown by a bold line in FIG. 5 is acquired by the actinometer as an optical spectrum of the B light at the time of causing the blue LED 23 to perform light emission alone with the maximum light amount value Lmax. FIG. 5 is a diagram showing an example of the optical spectra acquired when the blue LED provided in the light source device according to the embodiment is caused to perform light emission with the minimum light amount value Lmin and the maximum light amount value Lmax, respectively.

The factory operator performs work for capturing each of an optical spectrum of the R light with the minimum light amount value Lmin and an optical spectrum of the R light with the maximum light amount value Lmax acquired by the actinometer connected to the light source device 3 into a computer for factory work not shown (hereinafter, referred to merely as a computer). After that, by analyzing the two spectra of the R light captured from the actinometer connected to the light source device 3, the factory operator performs work for acquiring a correlation between the emitted light amount value LR of the red LED 21 and a mixed light amount value LRG which is a light amount of the R light mixed in the wavelength band GW in the case where only the red LED 21 is caused to perform light emission alone, using the computer. According to such work by the factory operator, a relational expression showing that the mixed light amount value LRG changes linearly relative to the emitted light amount value LR is acquired, for example, as shown in an equation (2) below and in FIG. 6.

Figure 6:
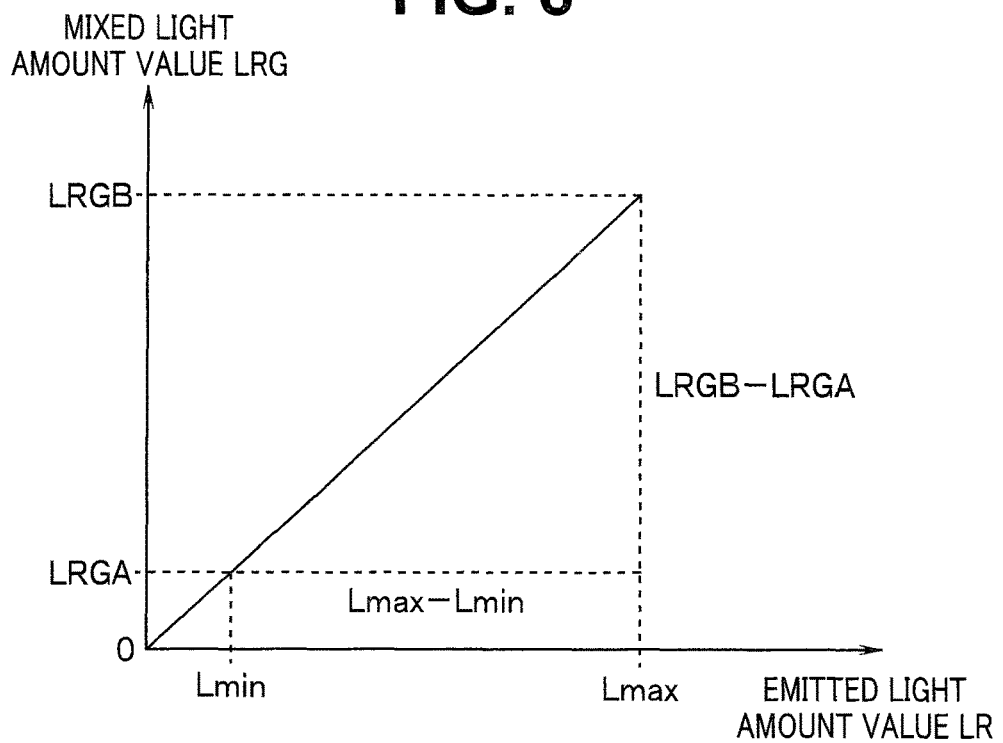
FIG. 6 is a diagram showing an example of a correlation between an emitted light amount value LR and a mixed light amount value LRG in the light source device according to the embodiment.

FIG. 6 is a diagram showing an example of the correlation between the emitted light amount value LR and the mixed light amount value LRG in the light source device according to the embodiment.

$$LRG = LR \times S \qquad (2)$$

Note that an inclination S included in the right side of the above equation (2) is a value calculated, for example, by performing arithmetic operation of (LRGB−LRGA)/(Lmax−Lmin) using a mixed light amount value LRGA corresponding to a light amount of lights with wavelengths equal to or shorter than the wavelength λgh included in the R light with the minimum light amount value Lmin and a mixed light amount value LRGB corresponding to a light amount of lights with wavelengths equal to or shorter than the wavelength λgh in the R light with the maximum light amount value Lmax (see FIG. 6). That is, the inclination S included in the right side of the above equation (2) indicates a ratio of an increased amount of the mixed light amount value LRG relative to an increased amount of the emitted light amount value LR.

Figure 7:
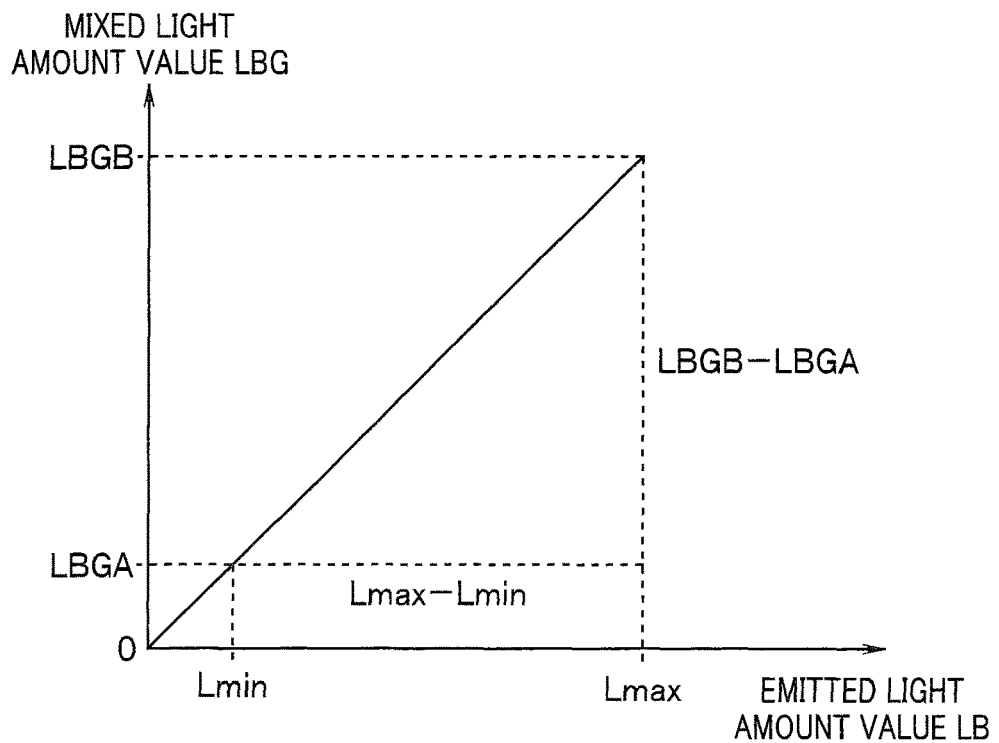
FIG. 7 is a diagram showing an example of a correlation between an emitted light amount value LB and a mixed light amount value LBG in the light source device according to the embodiment.

The factory operator performs work for capturing each of an optical spectrum of the B light with the minimum light amount value Lmin and an optical spectrum of the B light with the maximum light amount value Lmax acquired by the actinometer connected to the light source device 3 into the computer. After that, by analyzing the two spectra of the B light captured from the actinometer connected to the light source device 3, the factory operator performs work for acquiring a correlation between the emitted light amount value LB of the blue LED 23 and a mixed light amount value LBG which is a light amount of the B light mixed in the wavelength band GW in the case where only the blue LED 23 is caused to perform light emission alone, using the computer. According to such work by the factory operator, a relational expression showing that the mixed light amount value LBG changes linearly relative to the emitted light amount value LB is acquired, for example, as shown in an equation (3) below and in FIG. 7. FIG. 7 is a diagram showing an example of the correlation between the emitted light amount value LB and the mixed light amount value LBG in the light source device according to the embodiment.

$$LBG = LB \times T \qquad (3)$$

Note that an inclination T included in the right side of the above equation (3) is a value calculated, for example, by performing arithmetic operation of (LBGB−LBGA)/(Lmax−Lmin) using a mixed light amount value LBGA corresponding to a light amount of lights with wavelengths equal to or longer than the wavelength λgl included in the B light with the minimum light amount value Lmin and a mixed light amount value LBGB corresponding to a light amount of lights with wavelengths equal to or longer than the wavelength λgl in the B light with the maximum light amount value Lmax (see FIG. 7). That is, the inclination T included in the right side of the above equation (3) indicates a ratio of an increased amount of the mixed light amount value LBG relative to an increased amount of the emitted light amount value LB.

The factory operator calculates a total mixed light amount value ΔLG shown by an equation (4) below by performing arithmetic operation based on the above equations (2) and (3) (by the computer). That is, the total mixed light amount value ΔLG is calculated as a value corresponding to a sum of light amounts of the R light and the B light mixed in the wavelength band GW when the red LED 21, the green LED 22 and the blue LED 23 are simultaneously caused to perform light emission. The total mixed light amount value ΔLG is also calculated as a value that fluctuates according to the magnification α of the light amount of the R light when the light amount of the G light is assumed to correspond to once, and the magnification β of the light amount of the B light when the light amount of the G light is assumed to correspond to once.

$$\Delta LG = LRG + LBG = LR \times S + LB \times T = LG \times \alpha \times S + LG \times \beta \times T \qquad (4)$$

Here, for example, if the red LED 21, the green LED 22 and the blue LED 23 are caused to simultaneously perform light emission, a light amount obtained by adding the total mixed light amount value ΔLG to the emitted light amount value LG as shown by an equation (5) below, that is, the G light with an emitted light amount larger than the emitted light amount value LG corresponding to the G sensor detection value DG in the case where only the green LED 22 is caused to perform light emission alone is emitted from the light source device 3.

$$LG + \Delta LG = LG(1 + \alpha \times S + \beta \times T) \qquad (5)$$

Therefore, in the present embodiment, the G sensor characteristic information is corrected using such a correction variable making it possible to decrease the inclination A in the above equation (1) according to the magnitude of the total mixed light amount value ΔLG as the G sensor correction information so that, in the case of causing the red LED 21, the green LED 22 and the blue LED 23 to simultaneously perform light emission, a G sensor detection value DG according to the emitted light amount of the G light emitted from the light source device 3 can be obtained.

More specifically, in the present embodiment, such a correction variable Cg that causes a G sensor detection value DG obtained by the above equation (1) and a G sensor detection value DG obtained by an equation (6) below to be equal is acquired as the G sensor correction information.

$$DG = A \times Cg \times (LG + \Delta LG) + Q \qquad (6)$$

By performing arithmetic operation based on the above equations (1), (4) and (6) (by the computer), the factory operator acquires a correction variable Cg including two variables of the magnifications α and β as shown in an equation (7) below, and stores the acquired correction variable Cg into the memory 29a as the G sensor correction information.

$$Cg = LG/(LG + \Delta LG) = \qquad (7)$$
$$LG/\{LG(1 + \alpha \times S + \beta \times T)\} = 1/(1 + \alpha \times S + \beta \times T)$$

That is, according to the series of work performed at the time of manufacture or shipment inspection of the light source device 3 as described above, the G sensor characteristic information shown by the above equation (1) and the G sensor correction information shown by the above equation (7) are stored into the memory 29a. By work similar to the series of work as described above being performed at the time of manufacture or shipment inspection of the light source device 3, R sensor characteristic information acquired by a method similar to the method for the G sensor characteristic information and R sensor correction information, which is a correction variable Cr acquired by a method similar to the method for the correction variable Cg, are stored into the memory 29a. By work similar to the series of work as described above being performed at the time of manufacture or shipment inspection of the light source device 3, B sensor characteristic information acquired by a method similar to the method for the G sensor characteristic information and B sensor correction information, which is a correction variable Cb acquired by a method similar to the method for the correction variable Cg are stored into the memory 29a. Note that, in the present embodiment, since the optical spectrum of the R light overlaps only with the optical spectrum of the G light, such a correction variable Cr that does not include the magnification β is acquired. Further, in the present embodiment, since the optical spectrum of the B light overlaps only with the optical spectrum of the G light, such a correction variable Cb that does not include the magnification α is acquired.

By reading one piece of sensor characteristic information and one piece of sensor correction information stored in the memory 29a and correcting the one piece of sensor characteristic information using the one piece of sensor correction information and a light amount ratio RT, which is one of the light amount ratios R1 and R2, the arithmetic portion 29b acquires one piece of LED control information.

More specifically, the arithmetic portion 29b acquires a relational expression shown by an equation (8) below, for example, by multiplying the inclination A included in the G sensor characteristic information of the above equation (1) by the correction variable Cg included in the G sensor correction information of the above equation (7).

$$DG=\{A \times LG/(1+\alpha \times S+\beta \times T)\}+Q \quad (8)$$

The arithmetic portion 29b acquires a relational expression obtained by applying values corresponding to the magnifications α and β at the light amount ratio RT to the above equation (8) as the GLED control information.

Figure 8:
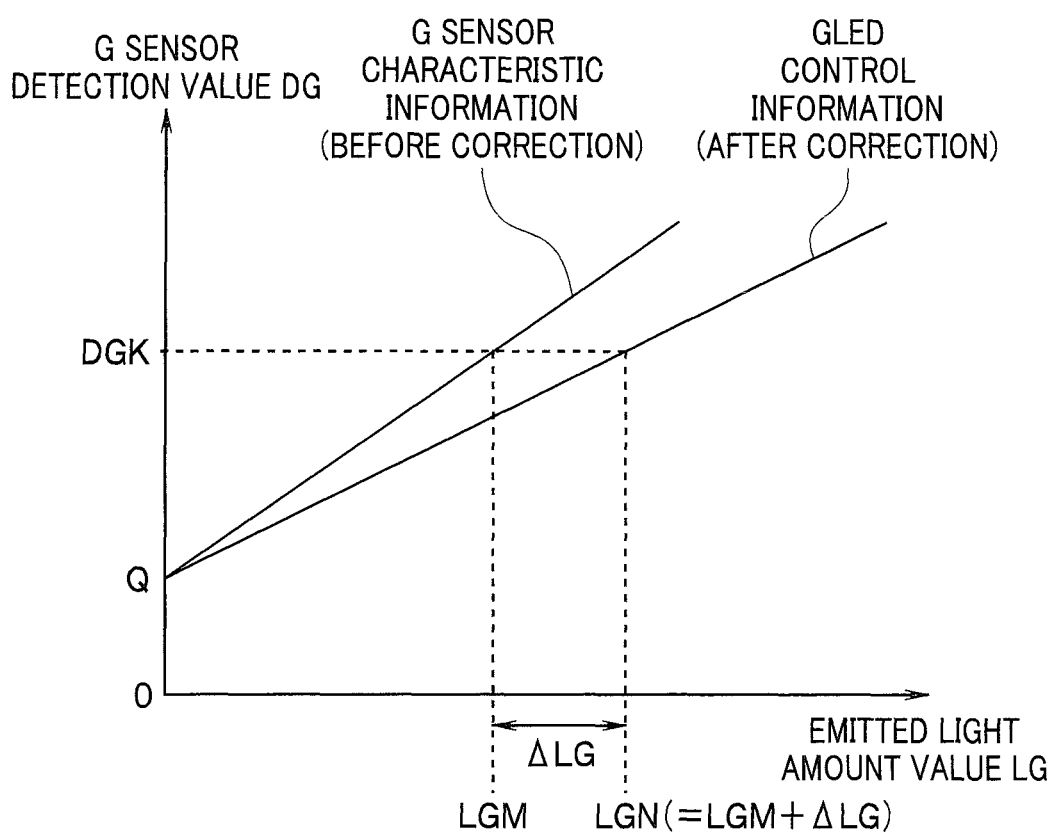
FIG. 8 is a diagram for illustrating an example of GLED control information obtained by correcting the G sensor characteristic information of the light source device according to the embodiment.

That is, according to the operation of the arithmetic portion 29b as described above, correction to set α light amount value obtained by adding the total mixed light amount value ΔLG to an emitted light amount value LGM corresponding to a G sensor detection value DGK in the G sensor characteristic information to an emitted light amount value LGN corresponding to the G sensor detection value DGK in the GLED control information, for example, as shown in FIG. 8. FIG. 8 is a diagram for illustrating an example of the GLED control information obtained by correcting the G sensor characteristic information of the light source device according to the embodiment.

The arithmetic portion 29b acquires RLED control information and BLED control information by correcting the R sensor characteristic information and the B sensor characteristic information using correction methods similar to the method of correcting the G sensor characteristic information as described above, respectively. Then, the arithmetic portion 29b acquires the RLED control information, the GLED control information and the BLED control information as light source control information.

That is, the arithmetic portion 29b acquires the GLED control information used to adjust the G light at the time of causing the red LED 21, the green LED 22 and the blue LED 23 to simultaneously perform light emission, by correcting the G sensor characteristic information using the correction variable Cg acquired based on the light amounts of the R light and the B light mixed in the wavelength band GW and the light amount ratio RT. Further, the arithmetic portion 29b acquires the RLED control information used to adjust the R light at the time of causing the red LED 21, the green LED 22 and the blue LED 23 to simultaneously perform light emission, by correcting the R sensor characteristic information using the correction variable Cr acquired based on the light amount of the G light mixed in the wavelength band RW and the light amount ratio RT. Further, the arithmetic portion 29b acquires the BLED control information used to adjust the B light at the time of causing the red LED 21, the green LED 22 and the blue LED 23 to simultaneously perform light emission, by correcting the B sensor characteristic information using the correction variable Cb acquired based on the light amount of the G light mixed in the wavelength band BW and the light amount ratio RT.

The controlling portion 29 performs control for causing the red LED 21, the green LED 22 and the blue LED 23 to simultaneously perform light emission, for the LED driving portion 28 in response to an instruction from the operation panel 27. The controlling portion 29 acquires an R sensor detection value, a G sensor detection value and a B sensor detection value based on light amount detection signals outputted from the optical sensors 21b, 22b and 23b, respectively. The controlling portion 29 acquires emitted light amount values of the red LED 21, the green LED 22 and the blue LED 23 according to brightness control information outputted from the image processing device 4, by applying the R sensor detection value, the G sensor detection value and the B sensor detection value to the light source control information obtained from the arithmetic portion 29b, respectively; and performs control for adjusting light amounts of the R light, the G light and the B light according to the acquired emitted light amount values, respectively, for the LED driving portion 28.

That is, at the time of causing the R light, the G light and the B light to be simultaneously emitted, the controlling portion 29 adjusts the G light, treating the light amounts of the R light and the B light mixed in the wavelength band GW as light amounts that fluctuate according to the light amount ratio RT, based on the GLED control information obtained from the arithmetic portion 29b. Further, at the time of causing the R light, the G light and the B light to be simultaneously emitted, the controlling portion 29 adjusts the R light, treating the light amount of the G light mixed in the wavelength band RW as a light amount that fluctuates according to the light amount ratio RT, based on the RLED control information obtained from the arithmetic portion 29b. Further, at the time of causing the R light, the G light and the B light to be simultaneously emitted, the controlling portion 29 adjusts the B light, treating the light amount of the G light mixed in the wavelength band BW as a light amount that fluctuates according to the light amount ratio RT, based on the BLED control information obtained from the arithmetic portion 29b.

Here, for example, if adjustment of emitted light amounts is performed without considering overlapping parts among the optical spectra of the R light, the G light and the B light while the red LED 21, the green LED 22 and the blue LED 23 are caused to simultaneously perform light emission, a problem occurs that white light with a light amount ratio different from an originally intended light amount ratio is supplied from the light source device 3 to the endoscope 2.

In comparison, according to the present embodiment, it is possible to adjust emitted light amounts while magnitudes of light amounts of the overlapping parts among the optical spectra of the R light, the G light and the B light are caused to fluctuate according to a light amount ratio among the R light, the G light and the B light. Therefore, according to the present embodiment, it is possible to supply white light with an originally intended light amount ratio from the light source device 3 to the endoscope 2, and it is possible to appropriately adjust color balance among the R light, the G light and the B light included in the white light.

Note that the present embodiment may be applied to light source devices other than the light source device 3 that generates lights of three colors, R light, G light and B light, as long as lights of two or more colors the optical spectra of which mutually overlap are generated. More specifically, for example, the present embodiment is almost similarly applied to a light source device that generates lights of five colors of R light, G light, B light, violet light and amber light.

Further, for example, the present embodiment is also almost similarly applied to a case where at least one of the respective LEDs provided in the light source device 3 is replaced with a laser diode.

According to the present embodiment, for example, when the controlling portion 29 performs control for causing a plurality of LEDs the optical spectra of which do not mutually overlap to simultaneously perform light emission in response to an instruction from the operation panel 27, the controlling portion 29 may use sensor characteristic information obtained at the time of causing each of the plurality of LEDs to perform light emission alone as LED control information as it is (without correction) to adjust each emitted light amount. More specifically, for example, at the time of performing control for causing the green LED 22 to perform light extinction and the red LED 21 and the blue LED 23 to simultaneously perform light emission in response to an instruction from the operation panel 27, the controlling portion 29 may adjust the emitted light amount of the red LED 21 using the R sensor characteristic information as the RLED control information as it is and adjust the emitted light amount of the blue LED 23 using the B sensor characteristic information as the BLED control information as it is.

According to the present embodiment, for example, when the controlling portion 29 performs control for causing the red LED 21, the green LED 22 and the blue LED 23 to perform light emission in a time division manner in response to an instruction from the operation panel 27, the controlling portion 29 may adjust the emitted light amount of the red LED 21 using the R sensor characteristic information as the RLED control information as it is, adjust the emitted light amount of the green LED 22 using the G sensor characteristic information as the GLED control information as it is and adjust the emitted light amount of the blue LED 23 using the B sensor characteristic information as the BLED control information as it is.

The present embodiment is almost similarly applied to the case where the R light, the G light and the B light are caused to be generated in a time division manner as long as lights of two or more colors the optical spectra of which mutually overlap are caused to be simultaneously generated. More specifically, for example, the present embodiment is almost similarly applied to such a case that control for causing the R light and the G light to be simultaneously generated and control for causing the G light and the B light to be simultaneously generated are alternately repeated.

By appropriately modifying the present embodiment, for example, information showing a correlation between a light amount indication value corresponding to brightness of one LED set according to an instruction from the operation panel 27 and a driving current value corresponding to the magnitude of a driving current of an LED driving signal supplied to the one LED from the LED driving portion 28 may be corrected to obtain control information used for adjustment of the light amount of the one LED.

According to the present embodiment, only sensor characteristic information corresponding to an LED of a particular color may be corrected instead of correcting sensor characteristic information corresponding to an LED of each color. In such a case, it is possible to appropriately adjust color balance of illumination light supplied from the light source device 3 to the endoscope 2 in comparison with the case of correcting the sensor characteristic information corresponding to the LED of each color.

According to the present embodiment, for example, a process for acquiring the RLED control information and the BLED control information by a method shown below may be performed by the arithmetic portion 29b. Note that, hereinafter, specific description of parts to which a configuration, an operation or the like already stated can be applied will be appropriately omitted for simplification.

When a value corresponding to a light amount of the G light mixed in the wavelength band RW when the red LED 21, the green LED 22 and the blue LED 23 are caused to simultaneously perform light emission is assumed to be the total mixed light amount value $\Delta LR$, a relationship of $LR+\Delta LR:LG+\Delta LG=\alpha:1$ is established. According to the relationship, the emitted light amount value LR of the red LED 21 can be indicated by an equation (9) below.

$$LR = \alpha \times (LG + \Delta LG) - \Delta LR = \alpha \times LG \times \{1 + \Delta LG/LG - \Delta LR/(\alpha \times LG)\} \quad (9)$$

According to the above equation (4), a relationship shown by an equation (10) below is established.

$$\Delta LG/LG = (LG \times \alpha \times S + LG \times \beta \times T)/LG = \alpha \times S + \beta \times T \quad (10)$$

Furthermore, in a case where the total mixed light amount value $\Delta LR$ linearly changes relative to the emitted light amount value LG, a relationship shown by an equation (11) below is established. Note that a value of P included in the equation (11) below is a value calculated by a method similar to the methods for the inclinations S and T stated before and indicates a ratio of an increased amount of the total mixed light amount value $\Delta LR$ relative to an increased amount of the emitted light amount value LG.

$$\Delta LR/(\alpha \times LG) = (LG \times P)/(\alpha \times LG) = P/\alpha \quad (11)$$

By applying each of the above equations (10) and (11) to the above equation (9), a relational expression shown by an equation (12) below can be obtained.

$$LR = \alpha \times LG \times (1 + \alpha \times S + \beta \times T - P/\alpha) \quad (12)$$

The arithmetic portion 29b acquires a relational expression obtained by applying values corresponding to the magnifications $\alpha$ and $\beta$ at the light amount ratio RT to the above equation (12) as the RLED control information. The controlling portion 29 adjusts the emitted light amount of the R light emitted from the red LED 21 by applying the emitted light amount value LG set using the GLED control information to the RLED control information.

That is, the arithmetic portion 29b acquires the RLED control information for adjusting the emitted light amount value LR at the time of causing the red LED 21 and the green LED 22 to simultaneously perform light emission according to the emitted light amount value LG set using the GLED control information, based on the total mixed light amount values ΔLG and ΔLR and the light amount ratio RT.

When a value corresponding to a light amount of the G light mixed in the wavelength band BW when the red LED 21, the green LED 22 and the blue LED 23 are caused to simultaneously perform light emission is assumed to be the total mixed light amount value ΔLB, a relationship of LB+ΔLB:LG+ΔLG=β:1 is established. According to the relationship, the emitted light amount value LB of the blue LED 23 can be indicated by an equation (13) below.

$$LB = \beta \times (LG + \Delta LG) - \Delta LB = \beta \times LG \times \{1 + \Delta LG/LG - \Delta LB/(\beta \times LG)\} \quad (13)$$

Furthermore, in a case where the total mixed light amount value ΔLB linearly changes relative to the emitted light amount value LG, a relationship indicated by an equation (14) below is established. Note that a value of U included in the equation (14) below is a value calculated by a method similar to the methods for the inclinations S and T stated before and indicates a ratio of an increased amount of the total mixed light amount value ΔLB relative to an increased amount of the emitted light amount value LG.

$$\Delta LB/(\beta \times LG) = (LG \times U)/(\beta \times LG) = U/\beta \quad (14)$$

By applying each of the above equations (10) and (14) to the above equation (13), a relational expression shown by an equation (15) below can be obtained.

$$LB = \beta \times LG \times (1 + \alpha \times S + \beta \times T - U/\beta) \quad (15)$$

The arithmetic portion 29b acquires a relational expression obtained by applying values corresponding to the magnifications α and β at the light amount ratio RT to the above equation (15) as the BLED control information. The controlling portion 29 adjusts the emitted light amount of the B light emitted from the blue LED 23 by applying the emitted light amount value LG set using the GLED control information to the BLED control information.

That is, the arithmetic portion 29b acquires the BLED control information for adjusting the emitted light amount value LB at the time of causing the green LED 22 and the blue LED 23 to simultaneously perform light emission according to the emitted light amount value LG set using the GLED control information, based on the total mixed light amount values ΔLG and ΔLB and the light amount ratio RT.

According to the method as described above, it is possible to obtain the RLED control information without correcting the R sensor characteristic information or without performing work for acquiring the R sensor characteristic information. According to the method as described above, it is possible to obtain the BLED control information without correcting the B sensor characteristic information or without performing work for acquiring the B sensor characteristic information.

Note that the present invention is not limited to the embodiment described above, and, of course, various changes and applications are possible within a range not departing from the spirit of the invention.

What is claimed is:

1. A light source device comprising:
   a first light source configured to generate first light having intensity in a first wavelength band and having a first optical spectrum;
   a second light source configured to generate second light having intensity in a second wavelength band adjoining to the first wavelength band and having a second optical spectrum overlapping with a part of the first optical spectrum;
   a first sensor configured to detect an emitted light amount of the first light source;
   a second sensor configured to detect an emitted light amount of the second light source; and
   a processor configured to:
      at a time of causing the first light source and the second light source to simultaneously perform light emission, cause the first light to be generated with a light amount adjusted according to a first mixed light amount which is a light amount of the second light mixed in the first wavelength band;
      at the time of causing the first light source and the second light source to simultaneously perform light emission, cause the second light to be generated with a light amount adjusted according to a second mixed light amount which is a light amount of the first light mixed in the second wavelength band;
      acquire first control information used to adjust a light amount of the first light at the time of causing the first light source and the second light source to simultaneously perform light emission by correcting first sensor characteristic information showing a correlation between an emitted light amount of the first light source in a case where the first light source is caused to perform light emission alone and a sensor detection value obtained according to the light amount detected by the first sensor, the correcting first sensor characteristic information being based on the first mixed light amount and a light amount ratio between the first light and the second light; and
      acquire second control information used to adjust a light amount of the second light at the time of causing the first light source and the second light source to simultaneously perform light emission by correcting second sensor characteristic information showing a correlation between an emitted light amount of the second light source in a case where the second light source is caused to perform light emission alone and a sensor detection value obtained according to the light amount detected by the second sensor, the correcting second sensor characteristic information being based on the second mixed light amount and the light amount ratio.

2. The light source device according to claim 1, further comprising:
   a memory storing information for setting the light amount ratio between the first light and the second light to a first light amount ratio; wherein
   the processor corrects each of the first sensor characteristic information and the second sensor characteristic information using the first light amount ratio if the processor cannot acquire information for setting the light amount ratio between the first light and the second light to a second light amount ratio different from the first light amount ratio from outside of the light source device, and corrects each of the first sensor characteristic information and the second sensor characteristic information using the second light amount ratio if the processor can acquire the information for setting the light amount ratio between the first light and the second light to the second light amount ratio from outside of the light source device.

3. The light source device according to claim 1, wherein at the time of causing the first light source and the second light source to perform light emission in a time division manner, the processor further adjusts the light amount of the first light using the first sensor characteristic information as the first control information as it is, and adjusts the light amount of the second light using the second sensor characteristic information as the second control information as it is.

4. The light source device according to claim 1, wherein the processor adjusts each of the light amount of the first light and the light amount of the second light based on the first control information, the second control information, and brightness control information acquired according to image brightness at a time of picking up an image of an object illuminated by the first light and the second light by an image processing device provided outside the light source device.

5. A light source device further comprising:
a first light source configured to generate first light having intensity in a first wavelength band and having a first optical spectrum;
a second light source configured to generate second light having intensity in a second wavelength band adjoining to the first wavelength band and a second optical spectrum overlapping with a part of the first optical spectrum;
a sensor configured to detect an emitted light amount of the first light source; and
a processor configured to:
at a time of causing the first light source and the second light source to simultaneously perform light emission, cause the first light to be generated with a light amount adjusted according to a first mixed light amount which is a light amount of the second light mixed in the first wavelength band;
acquire first control information used to adjust a light amount of the first light at the time of causing the first light source and the second light source to simultaneously perform light emission by correcting sensor characteristic information showing a correlation between an emitted light amount of the first light source in a case where the first light source is caused to perform light emission alone and a sensor detection value obtained according to the light amount detected by the sensor, the correcting sensor characteristic information being based on the first mixed light amount and a light amount ratio between the first light and the second light, and
acquire second control information for adjusting a light amount of the second light at the time of causing the first light source and the second light source to simultaneously perform light emission according to the light amount of the first light set using the first control information, based on the first mixed light amount, the second mixed light amount and the light amount ratio.

6. A light source device according to claim 1, comprising:
a first light source configured to generate first light having intensity in a first wavelength band and having a first optical spectrum;
a second light source configured to generate second light having intensity in a second wavelength band adjoining to the first wavelength band and a second optical spectrum overlapping with a part of the first optical spectrum;
a third light source configured to generate third light having a third optical spectrum having intensity in a third wavelength band adjoining to the second wavelength band and overlapping with a part of the second optical spectrum without overlapping with the first optical spectrum;
a processor; and
an operation panel capable of inputting, to the processor, a first instruction to cause the first light and the second light to be simultaneously emitted and a second instruction to cause the first light and the third light to be simultaneously emitted; wherein
the processor being configured to:
at a time of causing the first light source and the second light source to simultaneously perform light emission, cause the first light to be generated with a light amount adjusted according to a first mixed light amount which is a light amount of the second light mixed in the first wavelength band; and
cause the first light to be generated with the light amount adjusted according to the first mixed light amount and causes the second light to be generated with a light amount adjusted according to a second mixed light amount, which is a light amount of the first light mixed in the second wavelength band, when the first instruction is inputted from the operation panel, and causes the first light to be generated without performing light amount adjustment according to the first mixed light amount and causes the third light to be generated without performing light amount adjustment according to a third mixed light amount, which is a light amount of the second light mixed in the third wavelength band, when the second instruction is inputted from the operation panel.

7. An endoscope system comprising:
an endoscope configured to pick up an image of an object and output an image pickup signal; and
a light source device configured to supply illumination light for illuminating the object to the endoscope, the light source device comprising:
a first light source configured to generate first light having intensity in a first wavelength band and having a first optical spectrum;
a second light source configured to generate second light having intensity in a second wavelength band adjoining to the first wavelength band and having a second optical spectrum overlapping with a part of the first optical spectrum;
a first sensor configured to detect an emitted light amount of the first light source;
a second sensor configured to detect an emitted light amount of the second light source; and
a processor configured to:
at a time of causing the first light source and the second light source to simultaneously perform light emission, cause the first light to be generated with a light amount adjusted according to a first mixed light amount which is a light amount of the second light mixed in the first wavelength band;
at the time of causing the first light source and the second light source to simultaneously perform light emission, cause the second light to be generated with a light amount adjusted according to a second mixed light amount which is a light amount of the first light mixed in the second wavelength band;
acquire first control information used to adjust a light amount of the first light at the time of causing the first light source and the second light source to simultaneously perform light emission by correcting first sensor characteristic information showing a correlation between an emitted light amount of the first light source in a case where the first light source is caused to perform light emission alone and a sensor detection value obtained according to the light amount detected by the first sensor, the correcting first sensor characteristic information being based on the first mixed light amount and a light amount ratio between the first light and the second light; and acquire second control information used to adjust a light amount of the second light at the time of causing the first light source and the second light source to simultaneously perform light emission by correcting second sensor characteristic information showing a correlation between an emitted light amount of the second light source in a case where the second light source is caused to perform light emission alone and a sensor detection value obtained according to the light amount detected by the second sensor, the correcting second sensor characteristic information being based on the second mixed light amount and the light amount ratio.

8. A method of controlling a light source device for an endoscope, the light source device being configured to supply illumination light for illuminating an object to the endoscope configured to pick up an image of the object and output an image pickup signal, the method comprising:

generating first light having intensity in a first wavelength band and having a first optical spectrum;

generating second light having intensity in a second wavelength band adjoining to the first wavelength band and having a second optical spectrum overlapping with a part of the first optical spectrum;

detecting an emitted light amount of the first light;

detecting an emitted light amount of the second light;

at a time of simultaneously generating the first light and the second light, causing the first light to be generated with a light amount adjusted according to a first mixed light amount which is a light amount of the second light mixed in the first wavelength band;

at the time of simultaneously generating the first light and the second light, causing the second light to be generated with a light amount adjusted according to a second mixed light amount which is a light amount of the first light mixed in the second wavelength band;

acquiring first control information used to adjust a light amount of the first light at the time of simultaneously generating the first light and the second light by correcting first sensor characteristic information showing a correlation between an emitted light amount of the first light in a case where the first light is caused to perform light emission alone and a sensor detection value obtained according to the detected light amount of the first light, the correcting first sensor characteristic information being based on the first mixed light amount and a light amount ratio between the first light and the second light; and acquiring second control information used to adjust a light amount of the second light at the time of simultaneously generating the first light and the second light by correcting second sensor characteristic information showing a correlation between an emitted light amount of the second light in a case where the second light is caused to perform light emission alone and a sensor detection value obtained according to the detected light amount of the second light, the correcting second sensor characteristic information being based on the second mixed light amount and the light amount ratio.

9. An endoscope system comprising:

an endoscope configured to pick up an image of an object and output an image pickup signal; and a light source device configured to supply illumination light for illuminating the object to the endoscope, the light source device comprising:

a first light source configured to generate first light having intensity in a first wavelength band and having a first optical spectrum;

a second light source configured to generate second light having intensity in a second wavelength band adjoining to the first wavelength band and a second optical spectrum overlapping with a part of the first optical spectrum;

a sensor configured to detect an emitted light amount of the first light source; and a processor configured to:

at a time of causing the first light source and the second light source to simultaneously perform light emission, cause the first light to be generated with a light amount adjusted according to a first mixed light amount which is a light amount of the second light mixed in the first wavelength band;

acquire first control information used to adjust a light amount of the first light at the time of causing the first light source and the second light source to simultaneously perform light emission by correcting sensor characteristic information showing a correlation between an emitted light amount of the first light source in a case where the first light source is caused to perform light emission alone and a sensor detection value obtained according to the light amount detected by the sensor, the correcting sensor characteristic information being based on the first mixed light amount and a light amount ratio between the first light and the second light, and acquire second control information for adjusting a light amount of the second light at the time of causing the first light source and the second light source to simultaneously perform light emission according to the light amount of the first light set using the first control information, based on the first mixed light amount, the second mixed light amount and the light amount ratio.

10. A method of controlling a light source device for an endoscope, the light source device being configured to supply illumination light for illuminating an object to the endoscope configured to pick up an image of the object and output an image pickup signal, the method comprising:

generating first light having intensity in a first wavelength band and having a first optical spectrum;

generating second light having intensity in a second wavelength band adjoining to the first wavelength band and a second optical spectrum overlapping with a part of the first optical spectrum;

detecting an emitted light amount of the first light;

at a time of simultaneously generating the first light and the second light, causing the first light to be generated with a light amount adjusted according to a first mixed light amount which is a light amount of the second light mixed in the first wavelength band;

acquiring first control information used to adjust a light amount of the first light at the time of simultaneously generating the first light and the second light by correcting sensor characteristic information showing a correlation between an emitted light amount of the first light where the first light is generated alone and a sensor detection value obtained according to the detected light amount, the correcting sensor characteristic information being based on the first mixed light amount and a light amount ratio between the first light and the second light, and acquiring second control information for adjusting a light amount of the second light at the time of simultaneously generating the first light and the second light according to the light amount of the first light set using the first control information, based on the first mixed light amount, the second mixed light amount and the light amount ratio.

11. An endoscope system comprising:

an endoscope configured to pick up an image of an object and output an image pickup signal; and a light source device configured to supply illumination light for illuminating the object to the endoscope, the light source device comprising:

- a first light source configured to generate first light having intensity in a first wavelength band and having a first optical spectrum;
- a second light source configured to generate second light having intensity in a second wavelength band adjoining to the first wavelength band and having a second optical spectrum overlapping with a part of the first optical spectrum;
- a third light source configured to generate third light having a third optical spectrum having intensity in a third wavelength band adjoining to the second wavelength band and overlapping with a part of the second optical spectrum without overlapping with the first optical spectrum;
- a processor; and
- an operation panel capable of inputting, to the processor, a first instruction to cause the first light and the second light to be simultaneously emitted and a second instruction to cause the first light and the third light to be simultaneously emitted; wherein the processor being configured to:
- at a time of causing the first light source and the second light source to simultaneously perform light emission, cause the first light to be generated with a light amount adjusted according to a first mixed light amount which is a light amount of the second light mixed in the first wavelength band; and
- cause the first light to be generated with the light amount adjusted according to the first mixed light amount and causes the second light to be generated with a light amount adjusted according to a second mixed light amount, which is a light amount of the first light mixed in the second wavelength band, when the first instruction is inputted from the operation panel, and causes the first light to be generated without performing light amount adjustment according to the first mixed light amount and causes the third light to be generated without performing light amount adjustment according to a third mixed light amount, which is a light amount of the second light mixed in the third wavelength band, when the second instruction is inputted from the operation panel.

12. A method of controlling a light source device for an endoscope, the light source device being configured to supply illumination light for illuminating an object to the endoscope configured to pick up an image of the object and output an image pickup signal, the method comprising:

generating first light having intensity in a first wavelength band and having a first optical spectrum;

generating second light having intensity in a second wavelength band adjoining to the first wavelength band and having a second optical spectrum overlapping with a part of the first optical spectrum;

generating third light having a third optical spectrum having intensity in a third wavelength band adjoining to the second wavelength band and overlapping with a part of the second optical spectrum without overlapping with the first optical spectrum;

inputting a first instruction to cause the first light and the second light to be simultaneously emitted and a second instruction to cause the first light and the third light to be simultaneously emitted;

at a time of simultaneously generating the first light and the second light, causing the first light to be generated with a light amount adjusted according to a first mixed light amount which is a light amount of the second light mixed in the first wavelength band; and causing the first light to be generated with the light amount adjusted according to the first mixed light amount and causes the second light to be generated with a light amount adjusted according to a second mixed light amount, which is a light amount of the first light mixed in the second wavelength band, when the first instruction is input, and causing the first light to be generated without performing light amount adjustment according to the first mixed light amount and causing the third light to be generated without performing light amount adjustment according to a third mixed light amount, which is a light amount of the second light mixed in the third wavelength band, when the second instruction is input.

* * * * *